United States Patent
Moriarty et al.

(10) Patent No.: US 6,900,191 B1
(45) Date of Patent: May 31, 2005

(54) 1α-HYDROXYVITAMIN $D_5$, ITS SYNTHESIS AND USE IN CANCER PREVENTION

(75) Inventors: Robert M. Moriarty, Oak Park, IL (US); Raju A. Penmasta, Bolingbrook, IL (US); Liang Guo, Bolingbrook, IL (US); Munagala S. Rao, Westmont, IL (US); Rajendra G. Mehta, Orland Park, IL (US)

(73) Assignee: OncQuest, Inc., Chicago, IL (US)

( * ) Notice: Subject to any disclaimer, the term of this patent is extended or adjusted under 35 U.S.C. 154(b) by 1252 days.

(21) Appl. No.: 09/008,957

(22) Filed: Jan. 20, 1998

Related U.S. Application Data

(60) Provisional application No. 60/039,106, filed on Feb. 25, 1997.

(51) Int. Cl.[7] .................. A61K 31/59; C07C 401/00
(52) U.S. Cl. ........................ 514/167; 552/653
(58) Field of Search .................. 552/653; 514/167

(56) References Cited

U.S. PATENT DOCUMENTS

| | | | |
|---|---|---|---|
| 4,728,643 A | * 3/1988 | Holick et al. | 514/167 |
| 5,254,538 A | * 10/1993 | Holick et al. | 514/35 |
| 5,488,120 A | 1/1996 | Knutson et al. | |
| 5,700,790 A | * 12/1997 | Gulbrandsen et al. | 514/167 |
| 5,763,429 A | * 6/1998 | Bishop et al. | 514/168 |
| 5,869,472 A | 2/1999 | Moriarty et al. | |

OTHER PUBLICATIONS

Mehta, R.G.; Moriarty, R.M.; Mehta, R.R.; Penmasta, R.; Lazzaro, G.; Constantinou, A.; and Guo, L.; *Prevention of Preneoplastic Mammary Lesion Development by a Novel Vitamin D Analogue, 1α–Hydroxyvitamin $D_5$*, Feb. 5, 1997, Journal of the National Cancer Institute, vol. 89, No. 3, pp. 212–218.

* cited by examiner

Primary Examiner—Barbara P. Badio
(74) Attorney, Agent, or Firm—Clausen Miller, PC

(57) ABSTRACT

A compound of formula I:

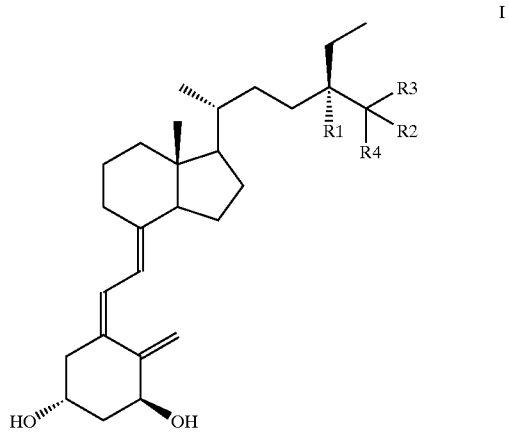

wherein R1 is hydrogen, R2 is —$CH_3$, R3 is —$CH_3$, and R4 is hydrogen, useful in cancer prevention and therapy.

1 Claim, 4 Drawing Sheets

13

13:   R1=H; R2=CH3; R3=CH3; R4=H

13a: R$_1$= H: R$_2$ = OH; R$_3$ = R$_4$ = CH$_3$

13b: R$_1$= OH: R$_2$ = H; R$_3$ = R$_4$ = CH$_3$

13c: R$_1$= OH: R$_2$ = OH; R$_3$ = R$_4$ = CH$_3$

13d: R$_1$= H: R$_2$ = OH; R$_3$ = R$_4$ = CF$_3$

13e: R$_1$= H: R$_2$ = H; R$_3$ = CH$_2$OH; R$_4$ = CH$_3$

1α-HYDROXYVITAMIN D₅, ITS SYNTHESIS AND USE IN CANCER PREVENTION

CROSS-REFERENCES TO RELATED APPLICATIONS

This application claims the benefit of U.S. Provisional Application Ser. No. 60/039,106 filed Feb. 25, 1997.

BACKGROUND OF THE INVENTION

1. Field of the Invention

This invention relates to biologically active vitamin $D_5$ compounds. More specifically, this invention relates to a series of novel $D_5$ compounds, including the compound 1α-Hydroxyvitamin $D_5$, their synthesis and their use in cancer prevention and therapy.

2. Description of the Related Art

Vitamin D is a secosteroid and is classified as a hormone within the steroid hormone family. Vitamin D's are differentiated on the basis of side-chain chemical structures into different series, e.g., $D_2$, $D_3$, $D_4$, $D_5$, and $D_6$. To date, attention has been focused almost exclusively on the vitamin $D_3$ series of compounds. In its biological form, vitamin $D_3$ is inactive until it is metabolized to 1α, 25-dihydroxyvitamin $D_3$ [1α, 25 $(OH)_2D_3$], the natural metabolite. The inactive 24-hydroxy form of the hormone is excreted from the body. The active metabolite 1α, 25 $(OH)_2D_3$ has been shown to suppress the growth in vitro of many neoplastic cells, including breast cancer cells. In addition, treatment of colon cancer cells and leukemia cells with 1α, 25 $(OH)_2D_3$ results in a reduction in the growth rate of these cells.

One of the limiting factors in the successful use of vitamin $D_3$ in cancer prevention or cancer therapy is its calcemic activity, i.e., the potentially fatal build-up of calcium in the body. The concentrations of vitamin $D_3$ required to suppress growth of neoplastic cells can cause hypercalcemia and death. Therefore, in recent years, numerous analogues of vitamin D have been synthesized that possess reduced calcemic activity without compromising their antiproliferative activity. The differences in structures of these new compounds arise mostly from modifications in the A and D rings and side chain of the vitamin.

We have synthesized the novel compound 1α-Hydroxyvitamin $D_5$ [1α(OH)$D_5$] and compared its effectiveness as a chemopreventative to the active metabolite of vitamin $D_3$. We have also attempted to determine the possible mechanism of such chemopreventative action by studying the expression of vitamin D receptors (VDRs) and transforming growth factor-β(TGF-β) in normal mammary epithelial cells.

SUMMARY OF THE INVENTION

This invention pertains to novel vitamin $D_5$ compounds including 1α-Hydroxyvitamin $D_5$, their synthesis, and a method for preventing and treating cancer using these compounds. 1α-Hydroxyvitamin $D_5$ has the following structure:

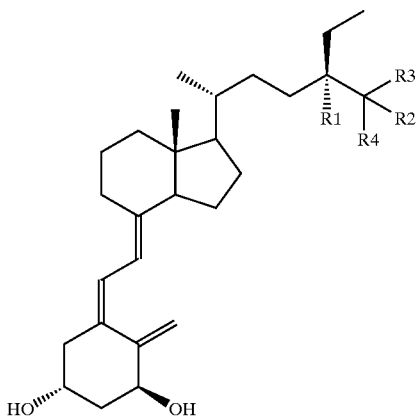

where $R_1 = R_4 = H$ and $R_2 = R_3 = CH_3$.

We have synthesized 1α-Hydroxyvitamin $D_5$ starting with a stigmasterol, although sitosterol may also be used as a starting material. Stigmasterol was converted to the 7-dehydro analogue and in turn to the vitamin $D_5$. The conversion of vitamin $D_5$ to 1α-Hydroxyvitamin $D_5$ was accomplished using literature procedures.

1α-Hydroxyvitamin $D_5$ is a white solid having a molecular formula of $C_{29}H_{48}O_2$ and a molecular weight of 428.7. The 1α-Hydroxyvitamin $D_5$ was fully characterized by $^1H$ NMR (400 Mhz), Mass Spectrum [CI], FTIR and UV. Purity was determined by straight and reverse phase high-pressure liquid chromatography (HPLC).

Usefulness of 1α-Hydroxyvitamin $D_5$: 1α-Hydroxyvitamin $D_5$ [1α(OH) $D_5$] is useful because it exhibits pharmacological activity in animals. In particular, preliminary studies in mice indicate 1α-Hydroxyvitamin $D_5$ is useful in preventing development of carcinogen-induced precancerous lesions at non toxic concentrations.

Use of 1α-Hydroxyvitamin $D_5$ in Cancer Prevention: Results show that the vitamin $D_5$ analogue 1α(OH)$D_5$ inhibits 7,12 dimethylbenz[a] anthracene (DMBA) induced mammary lesions in mammary gland organ culture. This assay has been used to predict possible chemopreventive agents in future clinical trials by the National Cancer Institute. The inhibitions of induction of lesions was accompanied by induction of vitamin D receptors and transforming growth factor β1.

1α-Hydroxyvitamin $D_5$ is less calcemic than a majority of the analogues of vitamin $D_3$. This will allow its possible use in prevention of cancer for women at high risk of developing cancer such as women with a family history of cancer or women who may be at a risk of developing disease in the contralateral breast. In addition to breast cancer prevention, the analogue 1α(OH)$D_5$ may be employed for prevention of cancers of other sites.

Use of 1α-Hydroxyvitamin $D_5$ in Cancer Therapy: Our studies showed that 1α(OH)$D_5$ inhibited growth of several human breast cancer cell lines, including ZR 75, T47D, MCF10neo, MCF-7, and BCA-4. The agent differentiates the cells making them less effective for forming cancers. Once the cells were differentiated with the analogue of $D_5$, they did not grow in athymic mice when transplanted. Similarly, injection of 8 mg of 1α(OH)$D_5$ (3 × week/2 months) to athymic mice bearing breast cancer cells inhibited growth of cancer cells in the animals. These results clearly suggest possible use of analogues of $D_5$ as chemotherapeutic agents or as adjuvants to chemotherapeutic protocol.

BRIEF DESCRIPTION OF THE DRAWINGS

The present invention will hereinafter be described in conjunction with the appended drawings.

DETAILED DESCRIPTION OF THE DRAWINGS

Figure 1:
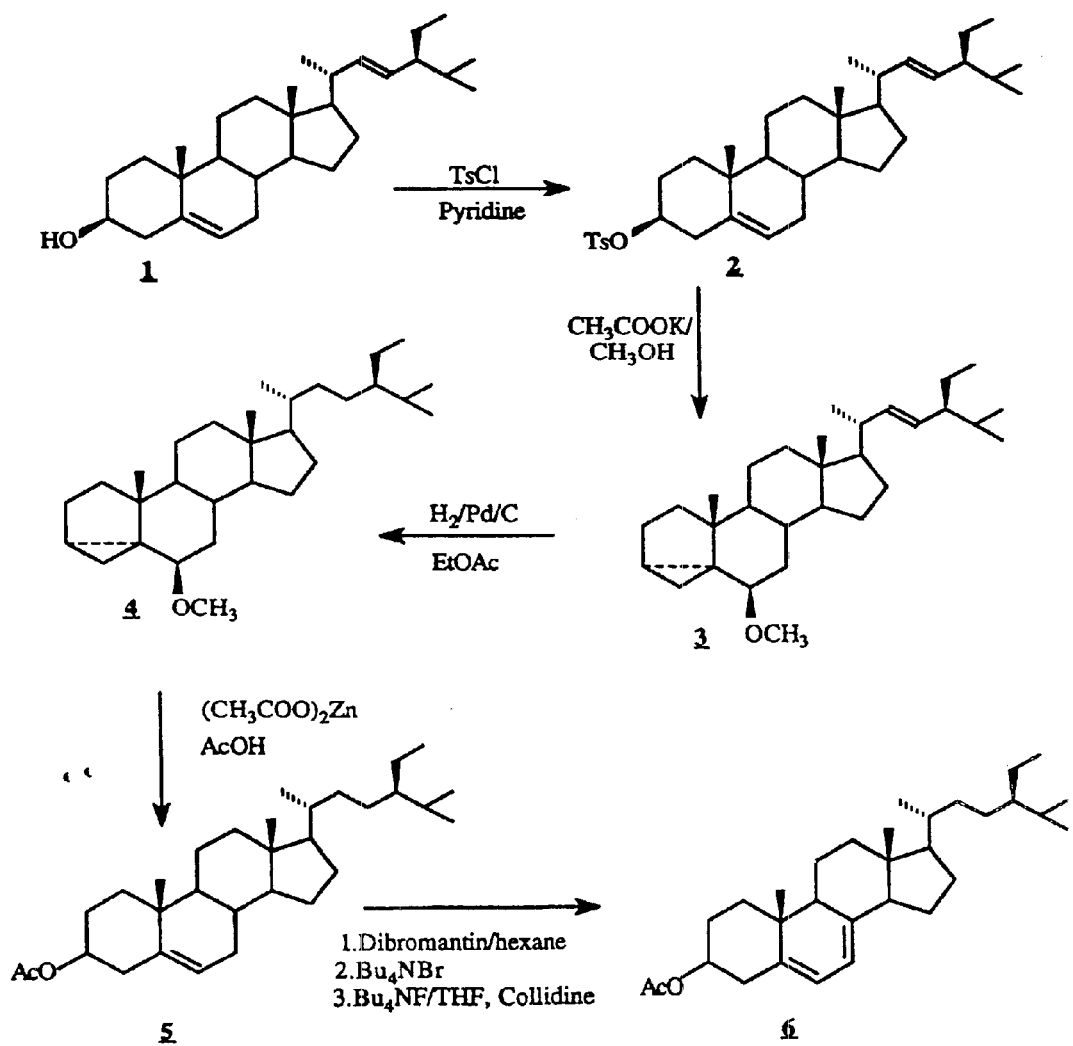
FIG. 1 illustrates the synthesis of 1α-Hydroxyvitamin $D_5$ from stigmasterol.
Figure 1:
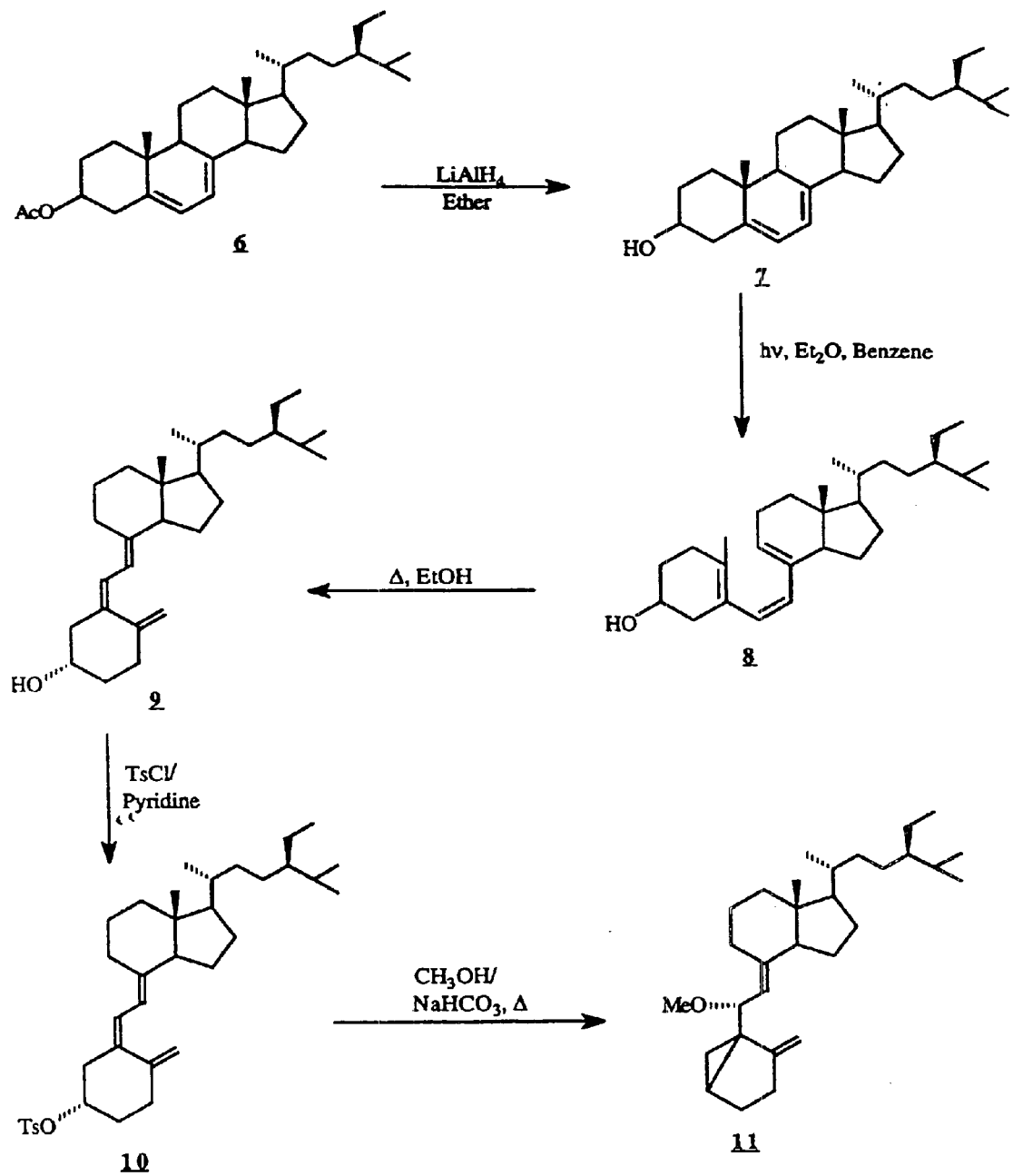
Figure 1:
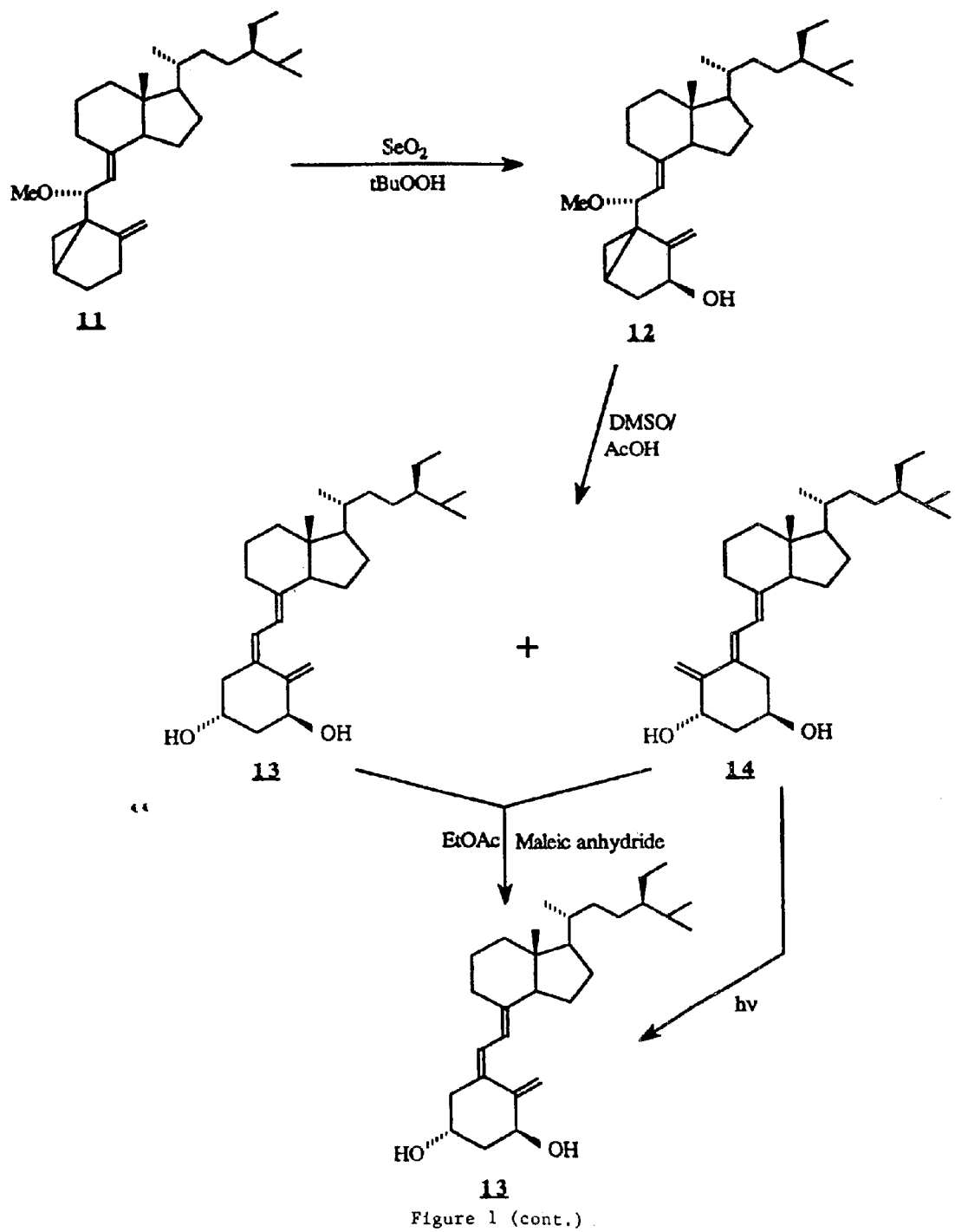

We have synthesized the novel compound 1α-Hydroxyvitamin $D_5$ and compared its calcemic activity, cancer prevention efficacy and toxicity to that of the active metabolite of vitamin $D_3$. We have also attempted to determine the possible mechanism of the chemopreventive activity of 1α-Hydroxyvitamin $D_5$ by studying the expression of VDRs and TGF-β1 in normal mammary epithelial cells.

I. SYNTHESIS OF 1α-Hydroxyvitamin $D_5$

1α-Hydroxyvitamin $D_5$ was prepared by the synthesis outlined in FIG. 1 and described in detail below. Numbers in parentheses refer to numerals in FIG. 1.

Step 1 - Preparation of stigmasterol tosylate (2): To a solution of stigmasterol (1) (50 g, 121.15 mmol) in anhydrous pyridine (400 ml) was added tosyl chloride (46.19 g, 242.3 mmol) under argon. The solution was stirred overnight at room temperature (20 hours) in the dark. The reaction mixture was poured into a 400 mL cold 5% $NaHCO_3$ solution. The pale crystalline precipitate was filtered, washed with water and air dried to yield 65 g (95%) of stigmasterol tosylate (2).

Step 2 - Preparation of stigmasterol methyl ether (3): A suspension of stigmasterol tosylate (2) (64 g, 112.9 mmol) and potassium acetate (70 g, 713.19 mmol) in anhydrous methanol (1500 mL) was refluxed for 4.5 h under argon atmosphere. The methanol was evaporated in vacuo, and then ether (2 L) was added, washed with water (500 mL), 5% $NaHCO_3$ (2×400 mL) and brine (400 mL) and dried ($MgSO_4$). The solvent was evaporated in vacuo to afford 47 g (92%) of stigmasterol methyl ether (3) as a pale yellow viscous liquid.

Step 3 - Preparation of sitosterol methyl ether (4): A solution of stigmasterol methyl ether (3) (10 g, 23.43 mmol) in ethyl acetate (250 mL) and 10% Pd-C (3 g) was shaken in Parr hydrogen apparatus for 4 h (30–40 psi). The Pd-C was filtered through Celite. The solvent was removed in vacuo to afford sitosterol methyl ether (4) in quantitative yield.

Step 4 - Preparation of Sitosterol acetate (5): To a solution of sitosterol methyl ether (4) (50 g, 116.62 mmol) in glacial acetic acid (1 L) was added zinc acetate (65 g, 354.3 mmol). The reaction mixture was refluxed for 6 h, cooled, then 1.5 L of water was added. The resulting white precipitate was filtered, washed with water and air dried. Recrystallization in ether-methanol afforded 42 g (79%) of sitosterol acetate (5) as a white crystalline solid.

Step 5 - Preparation of 7-Dehydrositosterol acetate (6): A suspension of sitosterol acetate (5) (10 g, 21.89 mmol), anhydrous $NaHCO_3$ (9.19 G, 109.45 mmol) and dibromantin in heptane (250 mL) was refluxed for 2 h under argon atmosphere. The reaction mixture was cooled to room temperature and filtered, and then the solvent was removed in vacuo. To the reaction flask, THF (50 mL) was added followed by tetrabutylammonium bromide (0.65 g, 2.02 mmol). The solution was stirred at room temperature for 30 minutes under argon atmosphere. To this reaction mixture tetrabutylammonium fluoride (112 mL, 1 M solution in THF) was added and followed by s-collidine (5 mL). Then the reaction mixture was stirred at room temperature for 20 h. The reaction mixture was diluted with ether (1.5 L), then water (600 mL) was added. The crude reaction mixture was transferred to a separating funnel, the water layer was removed, the organic layer was washed with water (500 mL), 1 N HCl (2×600 mL), water (600 mL), then brine (500 mL). The organic layer was dried ($MgSO_4$) and concentrated in vacuo to afford a dark brown viscous liquid. The crude reaction mixture was purified by column chromatography (silica gel, ethyl acetate-hexane 1:9 mixture as eluent) to afford 6.5 g, (75%) 7-dehydrositosterol acetate (6) as a pale brown viscous liquid.

Step 6 - Preparation of 7-Dehydrositosterol (7): To a solution of 7-dehydrositosterol acetate (6) (2.5 g, 5.5 mmol) in dry ether (200 mL) was added lithium aluminum hydride (2.09 g, 55.0 mmol). The reaction mixture was stirred at room temperature for 2 h, then cooled with an ice-water bath and the excess water (5 mL). After 30 minutes, ether (100 mL) was added and filtered. The cake was washed with ether (2×100 mL) and the combined organic extracts were dried ($MgSO_4$), filtered and concentrated in vacuo to afford 7-dehydrositosterol (7) in quantitative yield.

Step 7 - Preparation of Previtamin $D_5$ (8): 7-Dehydrositosterol (7) (1.5 g, 3.63 mmol) was dissolved in anhydrous ether (630 mL) and benzene (210 mL) and irradiated with stirring under argon in a water cooled quartz immersion well using a Hanovia medium-pressure mercury vapor lamp for 2 h. The reaction mixture was concentrated in vacuo to afford the crude previtamin $D_5$ as a pale brown viscous liquid. The crude reaction mixture was used without purification in the next step.

Step 8 - Preparation of Vitamin $D_5$ (9): 7-Dehydrositosterol (7) (1.5 g, 3.63 mmol) in ethanol (200 mL) was heated at 60° C. for 4 h. The reaction was monitored by TLC. The solution was concentrated in vacuo and the crude vitamin $D_5$ was purified on a silica gel column using 20% ethyl acetate in hexane to yield 600 mg (40%) of Vitamin $D_5$ (9).

Step 9 - Preparation of Vitamin $D_5$ tosylate (10): To a solution of Vitamin $D_5$ (9) (1.6 g, 3.88 mmol) in dry pyridine (20 mL) was added p-toluenesulfonyl chloride (2.22 g, 11.63 mmol). The reaction mixture was stirred under argon for 20 h at room temperature then poured into a cold saturated $NaHCO_3$ solution (100 mL). The mixture was extracted with ether (3×200 mL) and the combined organic extracts were washed with 5% HCl (2×200 mL), saturated sodium bicarbonate (2×200 mL) and brine (200 mL), dried ($MgSO_4$) and concentrated in vacuo to yield 2 g (98%) of Vitamin $D^5$ tosylate (10) as a brown viscous liquid.

Step 10 - Preparation of 3,5-Cyclovitamin $D_5$ (11): To a solution of Vitamin $D_5$ tosylate (10) (2 g, 3.53 mmol) in anhydrous methanol (250 mL) was added sodium bicarbonate (18 g, 214.26 mmol. The reaction mixture was heated under reflux for 8 h, then cooled and concentrated in vacuo. Water (300 mL) was added to the residue and the mixture was extracted with ether (2×300 mL). The combined organic extracts were washed with brine, dried ($MgSO_4$), filtered and concentrated in vacuo to yield 1.18 g (78%) of 3,5-cyclovitamin $D_5$ (11) as an oil.

Step 11 - Preparation of 1α-Hydroxy-3,5-Cyclovitamin $D_5$ (12): To a suspension of selenium dioxide (222 mg. 2 mmol) in dry methylene chloride (160 mL) was added t-butyl hydroperoxide (2.9 mL, 8 mmol, 3 M solution in toluene) under argon. The reaction mixture was stirred under argon at room temperature for 3 h, then dry pyridine (0.3 mL) was added followed by a solution of 3,5-cyclovitamin $D_5$ (11) (1.5 g, 3.52 mmol) in dry methylene chloride (50 mL). The reaction mixture was stirred at room temperature for 30 minutes, then 10% NaOH solution (60 mL) was added and the mixture was extracted with ether (3×250 mL). The combined organic extracts were washed with 10% NaOH solution (2×200 mL), water (2×200 mL) and brine (200 mL) and dried ($MgSO_4$) and concentrated in vacuo. The crude residue was purified by silica gel column chromatography using 20% ethyl acetate in hexane to yield 545 mg (35%) of 1α-hydroxy-3,5-cyclovitamin $D_5$ (12) as an oil.

Step 12 - Preparation of 1α-Hydroxyvitamin $D_5$ (13): A solution of 1α-hydroxy-3,5-cyclovitamin $D_5$ (12) (360 mg, 0.813 mmol) in DMSO (4 mL) and acetic acid (3.5 mL) was stirred and heated at 54–55° C. for 1 h under argon. The reaction mixture was poured into crushed ice (100 g), saturated $NaHCO_3$ (80 mL) was added to it, and the mixture was extracted with ether (3×150 mL). The combined organic extracts were washed with saturated $NaHCO_3$ solution (2×200 mL), water (2×150 mL) and brine (200 mL), dried ($MgSo_4$) and concentrated in vacuo, to yield 331 mg (95%) of a mixture of 1α-Hydroxyvitamin $D_5$ (13) and its 5,6-trans isomer (14).

Step 13 - Purification of 1α-Hydroxyvitamin $D_5$ (13): The crude reaction mixture of 1α-Hydroxyvitamin $D_5$ (13) and its 5,6-trans isomer (14) (320 mg, 0.75 mmol) was dissolved in ethyl acetate (70 mL) and then maleic anhydride (73 mg, 0.75 mmol) was added. The reaction mixture was stirred at 35° C. for 24 h under argon. The solution was concentrated in vacuo. The crude residue was purified on a silica gel column using 50% ethyl acetate in hexane to yield 150 mg (47%) of 1α-Hydroxyvitamin $D_5$ as a white solid. The compound (13) was crystallized from methylformate as white needles and further purified by HPLC (4.6×26 cm, C-18 column, $CH_3 CN:H_2O$ 9:1) to afford 80 mg of 1α-Hydroxyvitamin $D_5$ (13), >99% purity: mp 145–146° C.; IR (KBr): 3416 and 1638 $cm^{-1}$; UV ($CH_3OH$): λ $max^{265\ nm}$ (ε18,913); $^1H$ NMR ($CDCl_3$, 400 MHz) δ0.54 (S, 3H, 18-$CH_3$, 0.72-0.98 (m, 9H), 0.92 (d, 3H, J=6Hz, C21-$CH_3$), 4.24 (m, 1H, 1-H),4.43 (m, 1 H, 3-H), 5.0 (m, sharp, 1H, 19 (E) -H), 5.33 (m, sharp, 1H, 19 (Z) -H), 6.01 (d, 1H, J=11.3 Hz, 7-H), 6.38 (d, 1H, J-11.3 Hz, 6-H); MS (CI) m/e 429 ($M^+_+1$, 37%).

Figure 2:
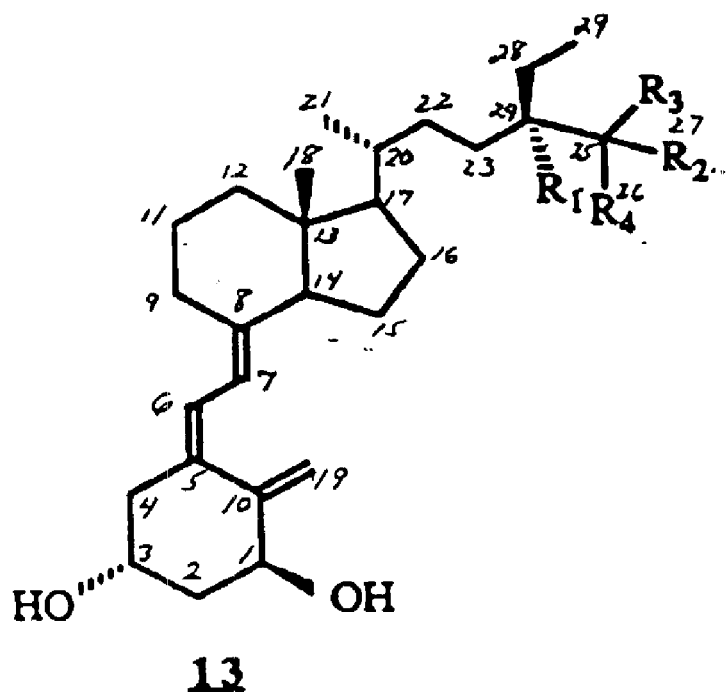
FIG. 2 illustrates the various analogues of 1α-Hydroxyvitamin $D_5$.

Thus the present invention provides the compound 1α-Hydroxyvitamin $D_5$ indicated by numeral (13) in FIGS. 1 and 2, and compounds (13a) –(13e) in FIG. 2 obtained from 1α-Hydroxyvitamin $D_5$ using literature procedures. In addition to the above compounds, the invention also provides compounds with stereochemistry at carbon centers $C_1$ (R or S), $C_3$ (R or S), $C_{20}$ (R or S) and $C_{24}$ (R or S) in FIG. 2.

II. COMPARISON OF CALCEMIC ACTIVITY, CHEMO-PREVENTIVE ACTIVITY, AND TOXICITY OF 1α-Hydroxyvitamin $D_5$ AND 1α, 25-DIHYDROVITAMIN $D_3$ A. Experimental Equipment and Methods 1. High-Pressure Liquid Chromatography (HPLC) Analysis of Vitamin D Analogues The vitamin $D_3$ and $D_5$ analogues were dissolved in acetonitrile at a final concentration of 0.2 mg/mL. Aliquots (10 µL) were injected on a Suplex PKB-100 HPLC column at ambient temperature. The HPLC was carried out with the use of an Hitachi L-6000 pump, an L-4200 UV-VIS detector, and an AS-2000 autosampler (Hitachi Instruments, Inc., Naperville, Ill.). The vitamin D analogues were eluted with the mobile phase of acetonitrile-methanol-water (52:30:18, vol/vol) with the flow rate at 1 mL/minute, and the elution profile was monitored at 254 nm.

Both 1α-Hydroxyvitamin $D_5$ and 1α, 25-dihydroxyvitamin $D_3$ analogues exhibited about 98% purity. Stability studies have suggested that both can be stored in powder form for a year at 20° C., whereas in solution they are stable for one month at the same temperature.

2. Measurement Of Calcemic Activity In Rats Administered Vitamin D Analogues

Three-week-old Sprangue-Dawley male rats were obtained from the Holtzman Laboratory, Madison, Wis. Up to three rats were housed together in a polycarbonate cage. The animal cages were kept under yellow light. The rats (eight to 10 per group per concentration of both vitamin D analogues used) were fed a vitamin D-free diet containing 0.47 g/100 g calcium and 0.3 g/100 g phosphorus. After the rats had consumed this diet for 3 weeks, their plasma calcium levels were measured. Rats exhibiting plasma calcium levels of less than 6.0 mg/dL were considered to be vitamin D deficient. Such rats were administered appropriate vitamin D analogues intragastrically for 14 days. At the end of this period, the plasma calcium levels were again measured.

3. Induction Of Preneoplastic Lesions In Mammary Glands And Their Prevention By Vitamin $D_3$ and $D_5$ Analogues Young, virgin BALB/c female mice, 3–4 weeks of age, were obtained from Charles River Laboratories, Wilmington, Mass. The mice were pretreated for 9 days with 17β-estradiol (1 µg in 0.1 mL saline per animal) and progesterone (1 mg in 0.1 mL saline per animal). They were then killed by cervical dislocation, and the thoracic pair of mammary glands was dissected out on silk rafts and incubated for 10 days in Waymouth MB752 medium (Life Technologies, Inc. [GIBCO BRL], Gauthersburg, Md.) containing the following growth-promoting hormones: insulin (5 µg/mL), prolactin (5 µg/mL), aldosterone (1 µg/mL), and hydrocortisone (1 µg/mL).

The carcinogen 7,12-dimethylbenz [a] anthracene (DMBA) at a dose of 2 µg/mL was added to the medium on day 3 for 24 hours to induce mammary lesions. The DMBA-containing medium was then removed, and the mammary glands were incubated for an additional 14 days with medium containing only insulin. This procedure allowed the normal glands to undergo structural regression in which all the normal alveolar structures were disintegrated. However, the alveolar lesions in the carcinogen-treated glands behaved differently. They had acquired altered hormone responsiveness, and these structures did not regress. These structures were termed "mammary lesions."

The vitamin D analogues (ranging in concentration from 0.01 μM to 10.0 μM) were included in the medium during the first 10 days of the in vitro culture to determine if they lowered the incidence of mammary lesion formation. Throughout the culture period, the glands were maintained at 37° C. in an environment of 95% air and 5% $CO_2$. At the end of the culture period, the glands were fixed in formalin, stained in alum-carmine solution, and evaluated for the presence or absence of mammary lesions. All hormones and chemicals were purchased from the Sigma Chemical Co., St. Louis, Mo.

4. Immunohistochemistry Of VDRs And TGF-β1

Normal mouse mammary glands were dissected and incubated with growth-promoting hormones either alone or in the presence of vitamin D analogues for only 3 days. In this experiment, the glands were not exposed to DMBA (see protocol described in the previous section). Instead, the glands were fixed in buffered formalin, and 5-μm-thick sections were prepared for histopathologic evaluations. The sections were mounted on adhesive-coated slides (Superfast: Fisher Scientific Co., Itasca, Ill.), dried at 60° C. for 1 hour, deparaffinized in xylene, dehydrated in a series of alcohol, and finally washed with phosphate-buffered saline (PBS).

To block the nonspecific antibody reactions, we treated the tissue sections with 5% dried skim milk for 10 minutes and then incubated them with primary mouse antibody (either against VDR or against TGF-β1, both obtained from BioGenex Laboratories, San Ramon, Calif.) overnight at 0–4° C. The tissues were rinsed in PBS and incubated with biotinylated rabbit anti-mouse antibody (Dako Corp., Carpenteria, Calif.) for 10 minutes; the remaining steps were followed according to the manufacturer-specified protocol; i.e., the reaction was stopped by rinsing the sections with PBS, which was followed by a 10 minute incubation with peroxidase-conjugated streptavidin, three 10-minute rinses with PBS, and a 5-minute incubation in a substrate, 3,3'-diaminobenzidine tetrachloride.

The tissues were counterstained with hematoxylin-eosin, dehydrated through graded series of alcohol and xylene, and finally mounted in Permount (Fisher Scientific Co.). Slides were evaluated for the presence or absence of the VDR or TGF-β1 and for the intensity of staining in the positively strained samples.

5. Statistical analysis

Statistical significance of the results was determined by the chi-squared test. All reported P values were obtained from two-sided tests.

B. Experimental Results

1. Calcemic Activity:

One of the primary reasons to synthesize new vitamin D agents is to prepare analogues that have reduced calcemic activity compared with that of $1\alpha, 25(OH)_2D_3$, but without compromising the antiproliferative activity. We measured the calcemic activity of both $1\alpha$-Hydroxyvitamin $D_5$ and $1\alpha, 25$-dihydroxyvitamin $D_3$.

As shown in Table 1, the vehicle-treated control rats showed a plasma calcium concentration of 5.4±0.28 mg/dL (mean ± standard deviation). When the rats were treated with the vitamin D analogues at a dose of 0.042 μg/kg per day, the following plasma calcium concentrations were observed: 6.0±0.63 mg/dL for $1\alpha(OH)D_5$-treated rats (an 11% increase over that of the vehicle-treated control group; P=.121, i.e., not statistically significant when compared with that of the control group) and 8.1±1.2 mg/dL for $1\alpha, 25(OH)_2D_3$-treated rats (a 50% increase over that of the control group; P=.002, i.e., statistically significant difference when compared with that of the control group). At a higher concentration of vitamin D analogues (0.25 μg/kg per day), $1\alpha(OH)D_5$ treatment resulted in a plasma calcium concentration of 7.9±1.5 mg/dL compared with 10.1±1.8 mg/dL for $1\alpha, 25 (OH)_2D_3$ treatment. Although both analogues at this concentration increased the plasma calcium levels in comparison with those in vehicle-treated control rats, these results showed that $1\alpha(OH)D_5$ has overall lower calcemic effects than $1\alpha, 25 (OH)_2D_3$.

$1\alpha, 25 (OH)_2D_3$ treatment resulted in an 87% increase in the plasma calcium level in rats when compared with the vehicle-treated rats. On the other hand, in animals treated with a higher concentration of $1\alpha(OH)D_5$, there was only a 50% increase in the plasma calcium concentration compared with that in the control animals. These results suggest that $1\alpha(OH)D_5$ is much less calcemic than $1\alpha, 25 (OH)_2D_3$.

TABLE 1

Effects of vitamin D analogues on plasma calcium levels in vitamin D-deficient rats

| Treatment[1] | No. of rats | Dose, μg/kg/day | Plasma calcium, mg/dL[2] | P (two-sided test) |
|---|---|---|---|---|
| None | 12 | 0.0 | 5.4 ± 0.28 | |
| $1\alpha(OH)D_5$ | 8 | 0.042 | 6.0 ± 0.63 | .121 |
|  | 10 | 0.25 | 7.9 ± 1.5 | .002 |
| $1\alpha,25(OH)_2D_3$ | 8 | 0.042 | 8.1 ± 1.2 | .001 |
|  | 10 | 0.25 | 10.1 ± 1.8 | <.0001 |

[1]$1\alpha(OH)D_5$ = $1\alpha$-Hydroxyvitamin $D_5$; $1\alpha,25(OH)_2D_3$ = $1\alpha,25$-dihydroxyvitamin $D_3$.
[2]Values = means +/− standard deviation.

2. Efficacy of Cancer Prevention

Traditionally, the effectiveness of a variety of chemopreventive agents has been evaluated by organ culture of the mouse mammary gland. In organ culture, mammary glands from mice respond to a short stimulation with a carcinogen in the presence of appropriate hormones by developing preneoplastic lesions. When implanted in syngeneic hosts, mammary cells prepared from these lesions give rise to adenocarcinomas. Effective chemopreventive agents (e.g., certain retinoids, selenium, oltipraz, and limonene) inhibit the formation of these lesions. The relative activity of chemopreventitive in vitro correlates well with their activity in in vivo carcinogenesis experiments. Using this traditional model system, we have evaluated the efficacy of $1\alpha$-Hydroxyvitamin $D_5$ [$1\alpha(OH)D_5$] in preventing 7,12-dimethylbenz [a]anthracene (DMBA)-induced mammary lesion formation in a mouse mammary gland organ culture model.

To evaluate the efficacy of the newly synthesized vitamin $D_5$ analogue in preventing mammary lesion formation, we incubated 15 mammary glands per group (135 glands in total) from BALB/c mice with appropriate hormones and exposed the glands to DMBA on day 3 for 24 hours (see "Experimental Equipment and Methods" section). The mammary glands were incubated for 10 days with the vitamin D analogues in concentrations ranging from 0.01 μM to 10.0 μM. The incidence of mammary lesions was calculated for each group and was reported as the ratio of the number of mammary glands showing lesions to the total number of mammary glands at risk.

Table 2 shows the incidence of mammary lesions in various groups treated with vitamin D analogues. In the vitamin $D_5$-treated group there was a dose-related decrease in the number of glands exhibiting lesions. In the group treated with vitamin $D_3$, only two of 14 glands developed lesions at a concentration of 0.01 μM. At higher concentrations of this analogue, no mammary lesions were observed.

We calculated the percent inhibition of formation of lesions in each treatment group by comparing the incidence of lesions between the control group and the treatment group. At a concentration of 10.0 μM, both $1\alpha(OH)D_5$ and $1\alpha, 25(OH)_2D_3$ inhibited the formation of mammary lesions by 100%.

At a concentration of 0.01 μM, the vitamin $D_3$ analogue inhibited mammary alveolar lesion formation by 76%; incubation of glands with concentrations of 0.1 μM and higher showed 100% inhibition. In contrast, the vitamin $D_5$ analogue inhibited the lesion formation in a dose-dependent manner, reaching 100% inhibition at a concentration of 10.0 μM.

TABLE 2

Effects of vitamin D analogues on incidence of 7,12 dimethylbenz[a]anthracene-induced lesions in BALB/c mouse mammary glands in organ culture

| Concentration (μM) | 1α-Hydroxyvitamin $D_5$ | | | 1,25α-dihydroxyvitamin $D_3$ | | |
| --- | --- | --- | --- | --- | --- | --- |
| | No. of glands with lesions/ total No. of glands treated | % incidence | P (two sided test) | No. of glands with lesions/ total No. of glands treated | % incidence | P (two sided test) |
| None | 9/15 | 60.0 | | 9/15 | 60.0 | |
| 0.01 | 6/16 | 37.5 | .21 | 2/14 | 14.3 | .011 |
| 0.1 | 4/16 | 25.0 | .048 | 0/15 | 0.0 | .003 |
| 1.0 | 2/14 | 14.3 | .011 | 0/15 | 0.0 | .003 |
| 10.0 | 0/15 | 0.0 | .003 | 0/15 | 0.0 | .003 |

3. Toxicity

To determine the effects of vitamin D analogues on the structural differentiation as well as their toxic effects on mammary glands, we incubated mammary glands with growth-promoting hormones for 3 days either alone or in the presence of 0.1 μM or 1.0 μM vitamin D analogues. The control mammary gland structure was represented by normal alveolar and ductal structures.

$1\alpha, 25(OH)_2D_3$ at a concentration of 0.1 μM did not show toxicity. Mammary glands displayed normal ductal and alveolar structures. At a concentration of 1.0 μM, vitamin $D_3$ analogue treatment resulted in disintegration of ducts and structural toxicity to the glands.

In contrast, treatment with the vitamin $D_5$ analogue at a concentration of 1.0 μM retained the healthy structural characteristics seen in the untreated glands. In fact, some secretion was obvious in the lumen of the ducts.

In summary, $1\alpha, 25(OH)_2D_3$ was toxic to the glands at concentrations of 1.0 μM or higher. Treatment of mammary glands with $1\alpha(OH)D_5$ did not result in any toxicity to the glands.

4. Mechanism of the Vitamin D Chemopreventive Activity

The mechanism of the vitamin D chemopreventive action is not completely understood. Nuclear vitamin D receptor (VDR) protein binding to $1\alpha, 25(OH)_2D_3$ has been identified and is shown to be present in a variety of tissues, including normal mammary glands and mammary tumors, as well as in breast cancer cells. In the cytosol of target organs or cells, $[^3H]1,25(OH)_2D_3$ binds specifically to receptors with a dissociation constant $(K_d)$ ranging from $1\times10^{-10}$ M to $6\times10^{-10}$ M. An increased nuclear VDR concentration has been found to be associated with an enhanced expression of messenger RNA for vitamin $D_3$ receptors. The VDR gene has been cloned, and the molecular structure of the receptor protein has been determined. The results have demonstrated that the VDR belongs to the steroid-, thyroid-, and retinoid-receptor superfamily. All of these receptors act as ligand-dependent transcription factors that bind to specific DNA sequences. Two classes of response elements have been identified that are activated either by VDR alone or by heterodimers of VDRs and retinoid X receptor (RXR) alpha.

In recent years, considerable attention has been given to the regulation of cell growth by autocrine antiproliferative factors. Inhibition of cancer cell growth is often related to enhanced production of transforming growth factor-β(TGF-β). TGF-β is further subclassified into the following three isoforms of polypeptides: TGF-β1, TGF-β2, and TGF-β3. These isoforms are present in mammalian cells, including breast cancer cells. The isoforms of TGF-β are regulated differentially by steroid and protein hormones. In one report, a hexafluoro analogue of vitamin $D_3$, 1α, 25-dihydroxy-16-ene-23-yne-26,27-hexafluorocholecalciferol (Ro24-5531), induced expression in HL-60 human leukemia cells of TGF-β1 and its type 2 receptors. These results suggest a possible interaction between the function of VDR and TGF-β regulation. Induction of TGF-β, however, is often reported only in transformed cells. Although the growth-inhibitory role of TGF-β has been reported in the normal mammary gland, induction of TGF-β in response to chemopreventive agents in this tissue has not been reported previously.

Since the role of chemopreventive agents (including vitamin $D_3$ and vitamin $D_5$) on the induction of TGF-β in normal mammary epithelial cells has not been studied, the histologic sections of normal mammary glands treated with either only hormones (insulin, progesterone, aldosterone, and hydrocortisone) or hormones plus vitamin D analogues were processed immunohistochemically to investigate the effects of vitamin D analogues on the induction and localization of VDRs and TGF-β1. VDRs were localized in the nuclei of mammary epithelial cells. There. was no selective localization of VDRs in ductal or alveolar cells. Treatment with either 1.0 μM $1\alpha(OH)D_5$ or 0.1 μM $1,25(OH)_2D_3$ induced expression of VDRs detectable in the nuclei of both ductal and alveolar cells. This induction was dependent on the concentration of the analogue; VDR induction was much less at the lower concentration of the vitamin $D_5$ analogue. For the vitamin $D_3$ analogue, intense staining was evident at a lower concentration (0.1 μM). However, at a concentration of 1.0 μM, reduced or absent staining was observed as a result of apparent toxicity.

The effects of the vitamin D analogues on the induction of TGF-β1 were also evaluated. We studied tissue sections from the mammary glands treated with the vitamin D analogues or those from untreated control glands for the induction of TGF-β1. We found extensive induction of TGF-β1 in the cytoplasm of mammary epithelial cells. Again, the pattern of intensity was comparable to that of induction of VDR. The extent of induction of TGF-β1 after treatment with the vitamin $D_5$ analogue at a concentration of 1.0 μM was similar to that observed with the vitamin $D_3$ analogue at a concentration of 0.1 μM. However, at a concentration of 1.0 μM of the vitamin $D_3$ analogue, TGF-β1 expression was much reduced as a result of toxicity. These results indicate that the vitamin $D_5$ analogue is considerably less toxic than the vitamin $D_3$ analogue. Moreover, they indicate that this remarkable induction of TGF-β1 in mammary epithelial cells by the vitamin $D_5$ analogue may be of importance in cancer chemoprevention.

Thus we have synthesized a novel vitamin $D_5$ compound and compared its calcemic activity, cancer prevention efficacy, and toxicity to that of vitamin $D_3$. We have found that 1α-Hydroxyvitamin $D_5$, while not completely devoid of calcemic activity, exhibited lower toxicity than 1α, 25-dihydroxyvitamin $D_3$. The present invention represents a first step toward the long-term goal of investigating the efficacy of chemoprevention by and the mechanism(s) of action of analogues of the vitamin $D_5$ series of compounds. Reduced calcemic activity and lack of toxicity make 1α-Hydroxyvitamin $D_5$ an attractive candidate for further in vivo chemoprevention studies.

We claim:

1. A compound of formula I:

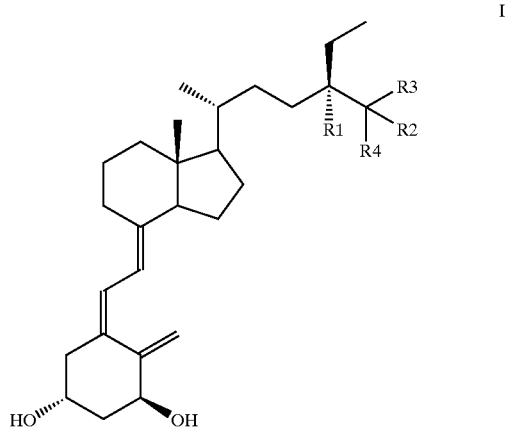

wherein:

R1 is hydrogen;

R2 is —CH$_3$;

R3 is —CH$_3$; and

R4 is hydrogen.

* * * * *